(12) United States Patent
Thomas et al.

(10) Patent No.: US 9,687,228 B2
(45) Date of Patent: *Jun. 27, 2017

(54) COATED LOOPED SUTURE

(71) Applicant: Covidien LP, Mansfield, MA (US)

(72) Inventors: Jonathan Thomas, New Haven, CT (US); Kenneth L. Martin, Wallingford, CT (US); Joseph Hotter, Delmar, NY (US); Darlene Nebinger, Oxford, CT (US); Ahmad Robert Hadba, Fort Worth, TX (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/603,564

(22) Filed: Jan. 23, 2015

(65) Prior Publication Data
US 2015/0157319 A1 Jun. 11, 2015

Related U.S. Application Data

(60) Continuation of application No. 14/078,945, filed on Nov. 13, 2013, now Pat. No. 8,979,894, which is a
(Continued)

(51) Int. Cl.
*A61B 17/06* (2006.01)
*A61L 17/14* (2006.01)
(Continued)

(52) U.S. Cl.
CPC ........ *A61B 17/06166* (2013.01); *A61L 17/12* (2013.01); *A61L 17/145* (2013.01);
(Continued)

(58) Field of Classification Search
CPC .............. A61B 17/04; A61B 17/06166; A61B 2017/06171; A61B 2017/06176; A61B 2017/0618; A61B 2017/06185; A61B 2017/0619; A61L 17/00; A61L 17/14; A61L 17/145
See application file for complete search history.

(56) References Cited

U.S. PATENT DOCUMENTS 2,514,184 A 7/1950 Lower
3,513,848 A 5/1970 Garvey
(Continued)

FOREIGN PATENT DOCUMENTS

EP 0870471 A1 10/1998
EP 1530951 A2 5/2005
(Continued)

OTHER PUBLICATIONS

European Search Report corresponding to European Application No. 12 16 3323.4-2310, dated Aug. 8, 2012 (7 pages).
(Continued)

*Primary Examiner* — Julian W Woo
*Assistant Examiner* — Shaun L David

(57) ABSTRACT

A suture including a reinforced loop is described herein. The suture includes an elongate body including a proximal section and a distal section, wherein the distal section includes first and second overlapping sections and a loop. A polymeric coating is positioned on at least a portion of the distal section to reinforce the loop.

20 Claims, 6 Drawing Sheets

Related U.S. Application Data division of application No. 13/045,618, filed on Mar. 11, 2011, now Pat. No. 8,968,362.

(60) Provisional application No. 61/322,106, filed on Apr. 8, 2010.

(51) Int. Cl.
 *A61L 17/12* (2006.01)
 *A61B 17/04* (2006.01)
 *A61B 17/00* (2006.01)

(52) U.S. Cl.
 CPC . *A61B 17/0401* (2013.01); *A61B 2017/00526* (2013.01); *A61B 2017/06176* (2013.01)

(56) References Cited

U.S. PATENT DOCUMENTS

| | | |
|---|---|---|
| 3,657,056 A | 4/1972 | Winston et al. |
| 3,858,245 A | 1/1975 | Nate, II et al. |
| 3,874,963 A | 4/1975 | Barger |
| 3,918,455 A | 11/1975 | Coplan |
| 4,662,068 A | 5/1987 | Polonsky |
| 4,932,962 A | 6/1990 | Yoon et al. |
| 4,950,285 A | 8/1990 | Wilk |
| 4,981,149 A | 1/1991 | Yoon et al. |
| 5,074,874 A | 12/1991 | Yoon et al. |
| 5,100,992 A | 3/1992 | Cohn et al. |
| 5,178,629 A | 1/1993 | Kammerer |
| 5,226,535 A | 7/1993 | Rosdhy et al. |
| 5,259,846 A | 11/1993 | Granger et al. |
| 5,290,284 A | 3/1994 | Adair |
| 5,330,491 A | 7/1994 | Walker et al. |
| 5,336,231 A | 8/1994 | Adair |
| 5,374,278 A | 12/1994 | Chesterfield et al. |
| 5,383,883 A | 1/1995 | Wilk et al. |
| 5,383,905 A | 1/1995 | Golds et al. |
| 5,395,382 A | 3/1995 | DiGiovanni et al. |
| 5,403,331 A | 4/1995 | Chesterfield et al. |
| 5,417,700 A | 5/1995 | Egan |
| 5,454,820 A | 10/1995 | Kammerer et al. |
| 5,458,582 A | 10/1995 | Nakao |
| 5,536,273 A | 7/1996 | Lehrer |
| 5,538,735 A | 7/1996 | Ahn |
| 5,540,703 A | 7/1996 | Barker, Jr. et al. |
| 5,628,756 A | 5/1997 | Barker, Jr. et al. |
| 5,633,343 A | 5/1997 | Bezwada et al. |
| 5,643,295 A | 7/1997 | Yoon |
| 5,665,109 A | 9/1997 | Yoon |
| 5,681,657 A | 10/1997 | Frey et al. |
| 5,683,417 A | 11/1997 | Cooper |
| 5,814,056 A | 9/1998 | Prosst et al. |
| 5,817,272 A | 10/1998 | Frey et al. |
| 5,830,234 A | 11/1998 | Wojciechowicz et al. |
| 5,863,654 A | 1/1999 | Frey et al. |
| 5,885,609 A | 3/1999 | Amiji |
| 5,893,880 A | 4/1999 | Egan et al. |
| 5,931,855 A | 8/1999 | Buncke |
| 5,964,765 A | 10/1999 | Fenton, Jr. et al. |
| 5,968,077 A | 10/1999 | Wojciechowicz et al. |
| 5,984,933 A | 11/1999 | Yoon |
| 6,077,277 A | 6/2000 | Mollenauer et al. |
| 6,089,438 A | 7/2000 | Suzuki et al. |
| 6,174,324 B1 | 1/2001 | Egan et al. |
| 6,183,499 B1 | 2/2001 | Fischer et al. |
| 6,217,591 B1 | 4/2001 | Egan et al. |
| 6,264,600 B1 | 7/2001 | Grimm |
| 6,286,746 B1 | 9/2001 | Egan et al. |
| 6,296,659 B1 | 10/2001 | Foerster |
| 6,348,152 B1 | 2/2002 | Kawahara et al. |
| 6,358,271 B1 | 3/2002 | Egan et al. |
| 6,409,743 B1 | 6/2002 | Fenton, Jr. |
| 6,435,190 B1 | 8/2002 | Taheri et al. |
| 6,488,690 B1 | 12/2002 | Morris et al. |
| 6,506,197 B1 | 1/2003 | Rollero et al. |
| 6,508,828 B1 | 1/2003 | Akerfeldt et al. |
| 6,517,578 B2 | 2/2003 | Hein |
| 6,599,310 B2 | 7/2003 | Leung et al. |
| 6,599,448 B1 | 7/2003 | Ehrhard, Jr. et al. |
| 6,613,059 B2 | 9/2003 | Schaller et al. |
| 6,669,705 B2 | 12/2003 | Westhaver et al. |
| 6,767,352 B2 | 7/2004 | Field et al. |
| 6,911,034 B2 | 6/2005 | Nobles et al. |
| 6,923,824 B2 | 8/2005 | Morgan et al. |
| 7,048,748 B1 | 5/2006 | Ustuner |
| 7,056,331 B2 | 6/2006 | Kaplan et al. |
| 7,090,111 B2 | 8/2006 | Egan et al. |
| 7,429,266 B2 | 9/2008 | Bonutti et al. |
| 7,533,791 B2 | 5/2009 | Steiner et al. |
| 7,582,097 B2 | 9/2009 | McRury et al. |
| 8,979,894 B2 | 3/2015 | Thomas et al. |
| 2002/0011508 A1 | 1/2002 | Egan et al. |
| 2002/0029065 A1 | 3/2002 | Shchervinsky |
| 2002/0058019 A1 | 5/2002 | Berenson et al. |
| 2003/0078603 A1 | 4/2003 | Schaller et al. |
| 2003/0162289 A1 | 8/2003 | Campbell et al. |
| 2003/0171761 A1 | 9/2003 | Sancoff et al. |
| 2003/0191355 A1 | 10/2003 | Ferguson |
| 2004/0087974 A1 | 5/2004 | Bittar |
| 2004/0122451 A1 | 6/2004 | Wood |
| 2004/0186340 A1 | 9/2004 | Reed et al. |
| 2004/0215208 A1 | 10/2004 | Foushee et al. |
| 2005/0107828 A1 | 5/2005 | Reese |
| 2005/0165448 A1 | 7/2005 | Egan et al. |
| 2005/0209639 A1 | 9/2005 | Gidwani et al. |
| 2005/0216058 A1 | 9/2005 | Egan et al. |
| 2005/0240225 A1 | 10/2005 | Schmieding et al. |
| 2005/0265488 A1 | 12/2005 | Jung |
| 2005/0267479 A1 | 12/2005 | Morgan et al. |
| 2005/0267531 A1 | 12/2005 | Ruff et al. |
| 2006/0025858 A1 | 2/2006 | Alameddine |
| 2006/0100544 A1 | 5/2006 | Ayala et al. |
| 2006/0111742 A1 | 5/2006 | Kaplan et al. |
| 2006/0135994 A1 | 6/2006 | Ruff et al. |
| 2006/0206096 A1 | 9/2006 | Accisano et al. |
| 2006/0259076 A1 | 11/2006 | Burkhart et al. |
| 2006/0282087 A1 | 12/2006 | Binmoeller |
| 2007/0021780 A1 | 1/2007 | Harrington et al. |
| 2009/0216269 A1 | 8/2009 | Harrington et al. |
| 2009/0248070 A1 | 10/2009 | Kosa et al. |
| 2009/0259251 A1 | 10/2009 | Cohen |
| 2010/0063540 A1 | 3/2010 | Maiorino |

FOREIGN PATENT DOCUMENTS

| | | |
|---|---|---|
| EP | 1656890 A2 | 5/2006 |
| EP | 1938762 A1 | 7/2008 |
| EP | 2163207 A1 | 3/2010 |
| EP | 2184157 A1 | 5/2010 |
| FR | 2729940 A1 | 8/1996 |
| JP | 09155979 | 6/1997 |
| WO | 9212673 A1 | 8/1992 |
| WO | 9625109 A1 | 8/1996 |
| WO | 9852473 A1 | 11/1998 |
| WO | 9921507 A2 | 5/1999 |
| WO | 9926542 A1 | 6/1999 |
| WO | 0222025 A1 | 3/2002 |
| WO | 03022161 A1 | 3/2003 |
| WO | 2006039217 A1 | 4/2006 |
| WO | 2006082586 A2 | 8/2006 |
| WO | 2007123943 A2 | 11/2007 |
| WO | 2008013864 A2 | 1/2008 |

OTHER PUBLICATIONS

European Search Report corresponding to European Application No. 12 16 3417.4-2310, dated May 31, 2012 (9 pages).

European Search Report corresponding to European Application No. 11 25 0441.0-1269, dated Jul. 29, 2011 (3 pages).

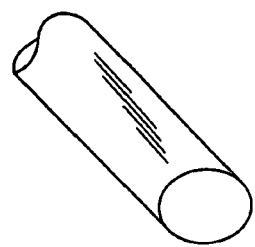
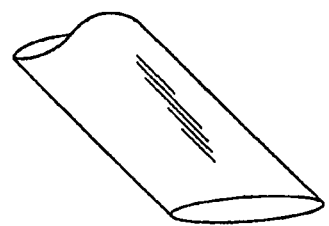
FIG. 2A  FIG. 2B
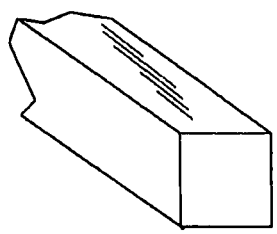
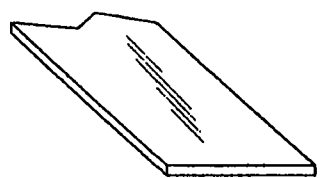
FIG. 2C  FIG. 2D
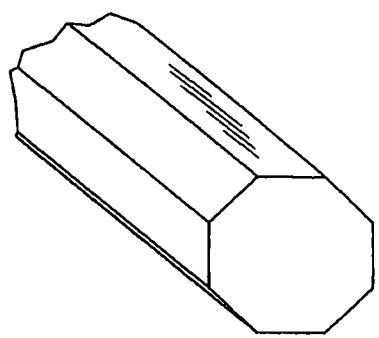
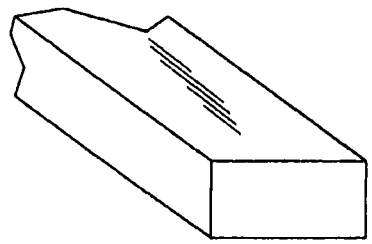
FIG. 2E  FIG. 2F

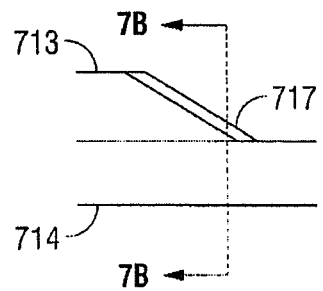 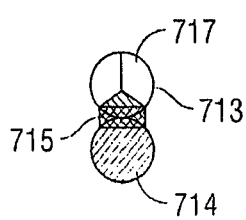 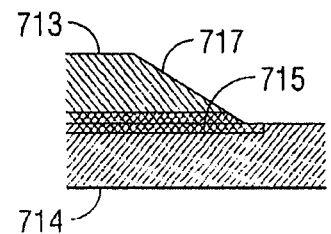
FIG. 7A  FIG. 7B  FIG. 7C
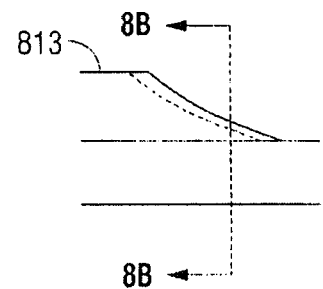 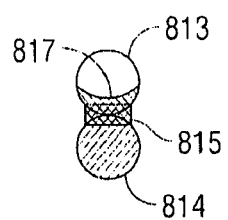 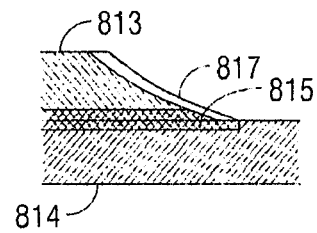
FIG. 8A  FIG. 8B  FIG. 8C
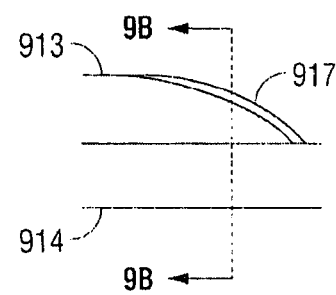 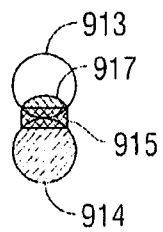 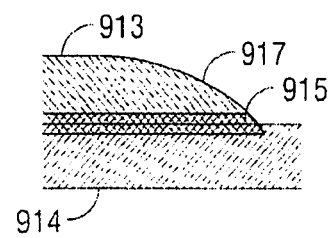
FIG. 9A  FIG. 9B  FIG. 9C

COATED LOOPED SUTURE

CROSS-REFERENCE TO RELATED APPLICATIONS

This present application is a continuation of pending U.S. application Ser. No. 14/078,945, filed Nov. 13, 2013, now U.S. Pat. No. 8,979,894, which is a divisional application of U.S. patent application Ser. No. 13/045,618, filed on Mar. 11, 2011, now U.S. Pat. No. 8,968,362, which claims the benefit of and priority to U.S. Provisional Application Ser. No. 61/322,106 filed on Apr. 8, 2010, the entire contents of each of which are incorporated herein by reference.

BACKGROUND

Technical Field

The present disclosure relates to a suture having a loop. More particularly, the present disclosure relates to a looped suture having a polymeric coating which reinforces the loop.

Background of Related Art

Sutures including loops formed therein are known. A loop formed in a suture during manufacture may be used to secure the suture to tissue. In this manner, once the non-looped end of the suture is inserted through tissue, that end may be threaded through the loop to form a slip knot-like configuration that may be tied to secure tissue. In another application, a loop may be formed in a suture in place of a knot. This requires the use of a handheld instrument that may be brought into an operating room.

Regardless of the reason for forming the loop, when a loop is formed in a suture, whether using adhesive, heat or ultrasonic energy, the loop may be under an inherent stress originating from the hairpin turn the suture makes in forming the loop. In the event that the suture loop is used to secure tissue, the holding power of the loop may be placed under increased stress while the tissue is healing. This increased stress applied to the loop may result in separation or the pulling apart of the loop.

Therefore, it would be beneficial to have a looped suture of enhanced loop stability.

SUMMARY

A suture including a loop is provided. The suture includes an elongate body including a proximal section and a distal section, wherein the distal section of the elongate body includes first and second overlapping sections and a loop. A distal aperture may be defined by the loop. A polymeric coating is positioned on at least a portion of the distal section to reinforce the loop.

The overlapping sections may be secured together to form the loop by at least one method selected from the group consisting of glues, adhesives, solvents, heat and ultrasonic energy. The loop may be sized and dimensioned to receive a length of the elongate body. The loop may be sized and dimensioned to receive a surgical needle.

In embodiments, the polymeric coating may be positioned on the first and second overlapping sections. In other embodiments, the polymeric coating may be positioned on at least a portion of the loop. In still other embodiments, the polymeric coating may be positioned across the distal aperture. In yet another embodiment, the polymeric coating may be positioned on the entire distal portion of the suture.

Also provided is a method of using a looped suture including a polymeric coating to reinforce the loop. The method includes the steps of providing a suture including an elongate body, and a loop formed on a distal end of the elongated body, wherein at least a portion of the distal end includes a polymeric coating to reinforce the loop, inserting a proximal end of the elongate body into tissue, and pulling the elongate body through the tissue until the loop engages the tissue.

The method further includes the step of inserting the proximal end of the elongate body through the loop. The suture may include a needle on the proximal end of the elongate body. The method may also include the step of tensioning the proximal end of the elongate body through the loop until the tissue is retained within the suture.

In another embodiment, methods of forming a reinforced looped suture are also described. The methods may include the steps of providing a suture having an elongate body including a proximal section and a distal section, wherein the distal section includes first and second overlapping sections, and a loop, and applying a polymeric coating to at least a portion of the distal section of the elongate body to reinforce the loop. In embodiments, the suture provided may also include a distal aperture defined by the loop. In embodiments, the polymeric coating may applied to at least one portion of the distal section including the first and second overlapping sections, the loop, the distal aperture and combinations thereof.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 2A-2F are perspective views of a suture having a circular (FIG. 2A), oval (FIG. 2B), rectangular (square) (FIG. 2C), flat (FIG. 2D), octagonal (FIG. 2E), and rectangular (FIG. 2F) cross-sectional profiles;

FIGS. 7A-7C are views of an alternate embodiment of a looped suture of the present disclosure;

FIGS. 8A-8C are views of yet another embodiment of a looped suture of the present disclosure;

FIGS. 9A-9C are views of still another embodiment of a looped suture of the present disclosure.

DETAILED DESCRIPTION

Figure 1A:
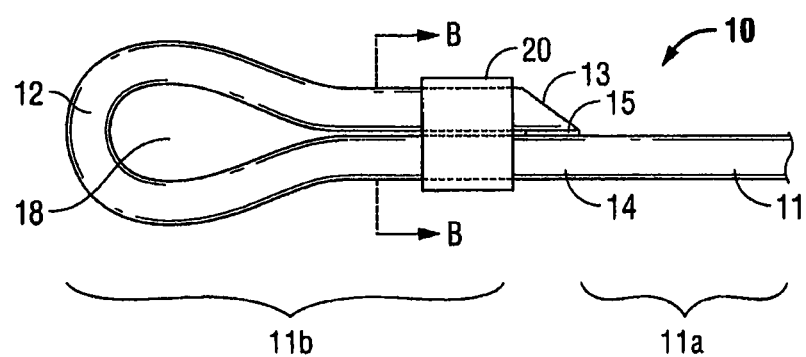
FIG. 1A is a side view of a looped suture in accordance with one embodiment of the present disclosure.

As shown in FIG. 1A, looped suture 10 includes elongate body 11 having proximal end 10a and distal end 10b. Proximal end 11a of elongate body 11 may include one or more suture needles (not shown). Distal end 11b of elongate body 11 includes first section 13 overlaying second section 14 to form loop 12. The adjacent surfaces of first and second sections 13, 14 form a joined segment or joint 15. Distal aperture 18 is defined within loop 12 which may form a substantially teardrop shape of any suitable size. In one embodiment, loop 12 is sized to receive proximal end 11a of looped suture 10. Polymeric coating 20 is shown positioned on at least a portion of distal end 11b to reinforce loop 12. In embodiments, polymeric coating 20 may be positioned on both first and second overlapping sections 13, 14 to reinforce joint 15 and loop 12, as depicted in FIG. 1B.

Figure 1B:
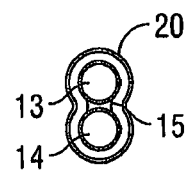
FIG. 1B is a cross-sectional end view of the looped suture taken along line B-B of FIG. 1A.

Although shown in FIGS. 1A and 1B as having a circular cross-sectional geometry, the cross-sectional geometry of elongate body 11 may be of any suitable shape. For example, FIGS. 2A-2F illustrate cross-sectional views of alternative embodiments of the various cross-sectional geometries of elongate body 11, namely, round (FIG. 2A), elliptical (FIG. 2B), square (FIG. 2C), flat (FIG. 2D), octagonal (FIG. 2E), and rectangular (FIG. 2F).

Sutures described herein may be formed from any sterilizable biocompatible material that has suitable physical properties for the intended use of the suture. The sutures described herein may be monofilaments or multifilaments sutures. The biocompatible materials may include biocompatible polymers, such as homopolymers or copolymers, including random copolymers, block copolymers, or graft copolymers. Biocompatible polymers may be a linear polymers, branched polymers or dendrimers.

Suitable polymers which may be used to construct sutures disclosed herein include, for example, synthetic materials, natural materials (e.g., biological) and combinations thereof. Suitable materials include, polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers and copolymers, such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins, such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof. Additionally, non-biodegradable polymers and monomers may be combined with each other to create a core of a fiber, for example a fiber possessing a core-sheath configuration.

Suitable bioabsorbable polymers may comprise implants of the present disclosure include, but are not limited to polymers selected from the group consisting of aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as such as poly (bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide)bioabsorbable polymers; and copolymers, block copolymers, homopolymers, blends, and combinations thereof.

More specifically, for the purpose of this invention, aliphatic polyesters include, but are not limited to, homopolymers and copolymers of lactide (including lactic acid, D-,L- and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Other suitable biodegradable polymers include but are not limited to poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

The looped sutures may be formed using any technique within the purview of those skilled in the art, such as, for example, extrusion, molding, casting and/or spinning. In some embodiments, the sutures may include a yarn made of more than one filament, which may contain multiple filaments of the same or different materials. Where the suture is made of multiple filaments, the suture may be made using any known technique such as, for example, braiding, weaving or knitting. The sutures may also be drawn, oriented, annealed, calendared, crinkled, twisted, commingled or air entangled to form yarns as part of the suture forming process. In one embodiment, a multifilament suture may be produced by braiding. The braiding may be done by any method within the purview of those skilled in the art.

Suture 10 includes loop 12 on distal portion 11b of elongate body 11. In embodiments, loop 12 may be formed during the formation of suture 10. In embodiments, loop 12 may be formed after the formation of suture 10.

In embodiments, loop 12 is formed by first and second sections 13, 14 forming joint 15 on distal section 11b of elongate body 11. First and second sections 13, 14 may form joint 15 using any suitable method known those skilled in the art. In one embodiment, first and second sections 13, 14 of elongate body 11 are welded together. In this manner, first and second sections 13, 14 of elongate body 11 are locally heated until each fuses to form joint 15. Various types of energy may be used to locally heat first and second sections 13, 14 to form joint 15, including, RF, ultrasonic, laser, electrical arc discharge, and thermal. Alternatively, first and second sections 13, 14 of elongate body 11 may be joined using glue, epoxy or other adhesive.

As depicted in FIG. 1A, polymeric coating 20 may be positioned on at least a portion of first and second sections 13, 14 of distal end 11*b* of elongate body 11 to reinforce loop 12. Polymeric coating 20 may be formed from any biocompatible polymeric material capable of maintaining the loop formation or enhancing the holding power of the loop. Some examples of useful biocompatible materials used to form polymeric coating 20 include, but are not meant to be limited to: polylactic acids (PLA); polyglycolic acids (PGA); poly-lactide-co-glycolide copolymers (PLGA); polytrimethylene carbonate (PTMC); poly-{acute over (.epsilon.)}-caprolactone (PCL); poly-dioxanone (PDO); polyhydroxyalkanoates such as polyhydroxybutyrate (P3HB, P4HB), polyhydroxyvalerate (PHV), poly(3-hydroxybutyrate-co-3-hydroxyvalerate) (PHBV), polyhydroxyoctanoate (PHO), and polyhydroxyhexanoate (PHH); polyphosphazenes; polypropylene fumarates; polyanhydrides; polyorthoesters; polyimides; perfluoroalkoxy polymers (PFAs); florinated ethylene/propylene copolymers (FEP); polyanhydride esters; polyurethanes including polyether urethanes, polyester urethanes, polycarbonate urethanes, polyether ureas, polyester ureas, polycarbonate ureas and combinations thereof, polysaccharides including cellulose, carboxymethylcellulose, chitosan, chitin, alginate, hyaluronic acid, fucans, and dextran; soybean protein; polyethylene-lactone copolymers; polyethylene-polyorthoester copolymers; polymer drugs; synthetic materials including hydrophilic vinyl polymers, phosphoryl cholines, hydroxamates, vinyl furanones, quarternary ammoniums, and alkylene oxides; biopolymers made from collagen, gelatin, elastin, keratin, fibrin, thrombin, and the like; and blends, copolymers, homopolymers, and combinations thereof.

In embodiments, the biocompatible materials used to form polymeric coating 20 may be combined with a solvent to form a liquid polymer composition prior to being applied to distal end 11*b* of elongate body 11 of suture 10. The liquid polymer composition may be a solution, suspension, emulsion dispersion, and the like. In embodiments, the liquid polymer composition may be a solution. The polymer solution may include from about 0.1% to about 30% polymeric material by weight and at least one solvent. Any variety of solvents may be suitable for forming the polymer solution. Examples of suitable solvents include but are not limited to at least one of the following: pentane, cyclopentane, hexane, cyclohexane, benzene, toluene, xylene, mesitylene, 1,4-dioxane, chloroform, diethyl ether, dichloromethane, tetrahydrofuran, 1,1,2-trichloroethane, trifluoroethanol, methyl acetate, ethyl acetate, amyl acetate, acetone, dimethylformamide, acetonitrile, dimethylsulfoxide, formic acid, n-butanol, isopropanol, ethanol, n-propronal, methanol, acetic acid, water, methylene chloride, cyclohexanone, ethyl formate, 2,2,2-trifluoroethanol, 2,2,3,3-tetrafluoro-1-propanol, 1,3-difluoro-2-propanol, 1,1,1,3,3,3-hexafluoro-2-methyl-2-propanol, 1,1,1,3,3,3-hexafluoro-2-propanol, 2,2,3,3,3-pentafluoro-1-propanol, nitroethane and combinations thereof.

In addition, polymer solutions may include at least one optional ingredient such as emulsifiers, viscosity enhancers, dyes, pigments, fragrances, pH modifiers, bioactive agent, wetting agent, plasticizers, antioxidants, and the like.

Alternatively, neat monomers, prepolymers or solutions of these, prepolymers hereon, can be used to form the polymeric coatings in situ. These prepolymers may be polymerized or crosslinked to form the final coating. Examples of monomers suitable for this application include cyanoacrylates, methyl methacrylate, methacrylate functional silicone oligomers, low Tg acrylates, acrylate or methacrylate functional polyurethanes, n-vinyl pyrrolidone (NVP), acrylic acid (AA), methacrylic acid (MAA), 2-hydroxyethyl methacrylate (HEMA), 2-acrylamido-2-methyl-1-propanesulfonic acid (AMPS), 2-(Dimethylamino)ethyl methacrylate (DMAEMA), n-(tris(hydroxymethyl)methyl) acrylamide (Tris acryl), acryl amide, 2-(methacryloyloxy) ethyl succinate, [2-(methacryloyloxy)ethyl]trimethylammonium methyl sulfate, and mixtures thereof. Crosslinking agents include dietheyleneglycol diacrylate, ethylene glycol dimethacrylate, 1,3-divinyltetramethyldisiloxane, divinyl benzene, and the like. The polymerization may be initiated with moisture in the case of cyanoacrylate. The polymerization may be initiated using heat sensitive initiators such as 4,4'-azobis(4-cyanovaleric acid) (ACVA), 2,2'-azobisisobutyronitrile (AIBN), 2,T-azobis(2-methylproprionamidine) dihydrochloride (AMPA), benzoyl peroxide (BPO) and the like. More preferentially, the polymerization may be initiated using light sensitive initiators such as benzophenone (BP), methylbenzoylformate (MBF), 2-benzyl-2-(dimethylamino)-4'-morpholinobutyrophenone (BDMB), 2,2'-dimethoxy-2-phenyl acetophenone (DMPA), 1-[1-(2-hydroxyethoxy)phenyl]-2-hydroxy-2-methyl-1-propan-1-one, and the like. In other embodiments, prepolymers such as B-staged polyurethanes, 2 part silicones and the like, may used to form the coating in situ. The coating is then fully cured using heat, light, or moisture depending on the underlying chemistry.

The polymer coating may be applied to the distal section of the suture using any suitable method including spraying, dipping, brushing, rolling, wiping, painting, extruding, ultrasonics, and the like. In embodiments, the looped suture may be dipped into a polymer solution. In some embodiments, the polymer solution may be sprayed onto the looped suture.

The polymer solution may be applied to any portion of the distal end of the suture suitable to reinforce the loop. Following the application of the solution to the suture, the sutures may be allowed to dry using any suitable drying method. Some non-limiting examples include drying under ambient conditions, within an oven, under vacuum, or forced air. Solvents having a lower boiling point may dry faster. The entire distal section of the elongate body may be dipped into the polymer solution and allowed to dry to form a polymeric coating which is positioned on the entire distal portion of the suture including both the loop and the first and second overlapping sections.

Figure 3:
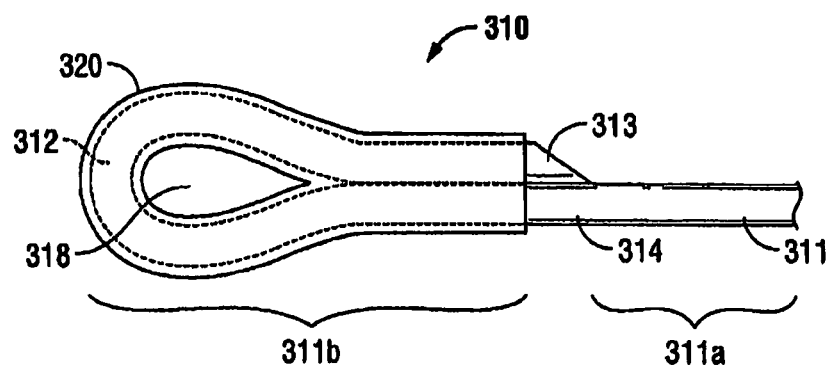
FIG. 3 is a side view of a looped suture in accordance with one embodiment of the present disclosure.

As depicted in FIG. 3, suture 310 includes elongate body 311 having distal end 311*b* which includes first section 313 overlaying second section 314 to form loop 312 (phantom). Polymeric coating 320 is positioned on loop 312 and a portion of first and second overlapping sections 313, 314. Distal aperture 318 is defined within loop 312 which allows proximal end 311*a* of suture 310 to pass through distal aperture 318 without passing through polymeric coating 320. In some embodiments, distal aperture may be created through the use of a punch (not shown).

Figure 4:
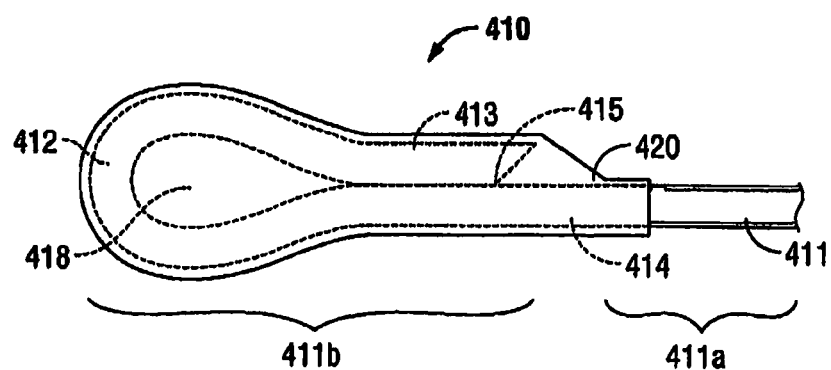
FIG. 4 is a side view of a looped suture in accordance with an alternate embodiment of the present disclosure.

In some embodiments, as shown in FIG. 4, polymeric coating 420 is positioned along loop 412 (phantom) and across distal aperture 418 (phantom). In such embodiments, polymeric coating 420 may form a film or web of sufficient thickness and/or elasticity to span the opening of distal aperture 418. In embodiments, proximal end 411*a* may pierce the web of polymeric coating 420 when passed through distal aperture 418 to close wound tissue. In embodiments, polymeric coating 420 may completely cover distal end 411b of elongate body 411, including first and second overlapping sections 413, 414, joint 415, loop 412, and distal aperture 418.

Figure 5:
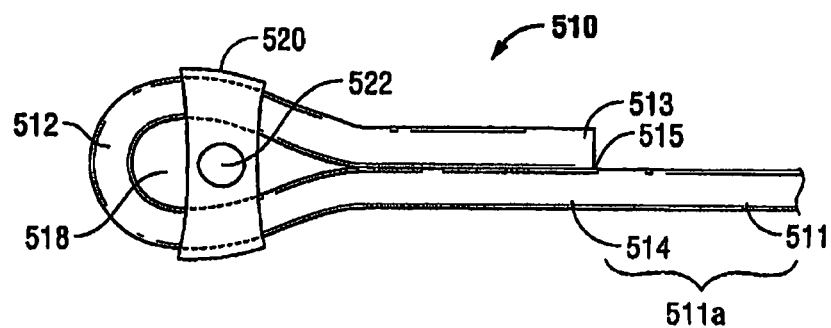
FIG. 5 is a side view of a looped suture in accordance with another embodiment of the present disclosure.

Alternatively, as shown in FIG. 5, polymeric coating 520 may be positioned along only a portion of loop 512 and across only a portion of distal aperture 518. In such embodiments, a portion of distal aperture 518 remains open for passage of proximal section 511a of suture 510. First and second overlapping sections 513, 514 and joint 515 of elongate body 511 may not include polymeric coating 520. In some embodiments, polymeric coating 520 may include coating aperture 522 which may also allow for the passage of proximal section 511a of suture 510. Coating aperture 522 is shown as an opening created in the web of polymer coating 520 which spans distal aperture 518. Such an opening may be formed during the manufacturing of the coated loop suture or may be formed after being pierced with proximal end 511a or surgical needle (not shown) attached to proximal end 511a.

Figure 6:
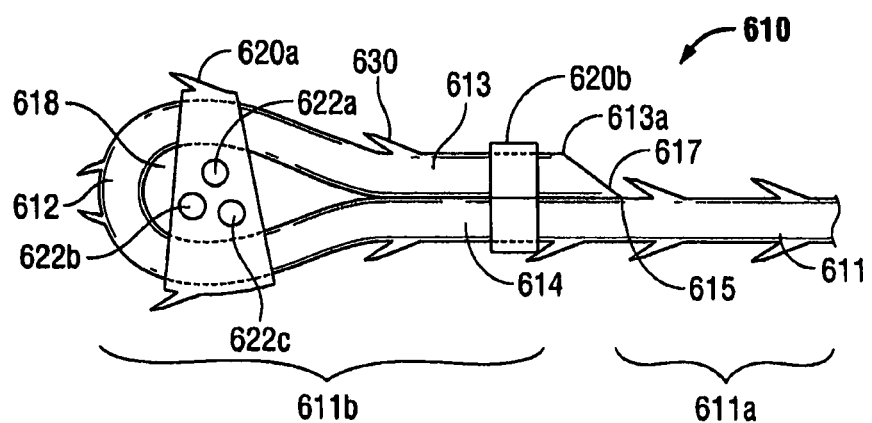
FIG. 6 is a side view of a looped suture in accordance with yet another embodiment of the present disclosure.

Turning now to FIG. 6, suture 610 may include barbs 630 and/or multiple polymeric coatings, i.e., first polymeric coating 620a and second polymeric coating 620b. It is envisioned that barbs 630 may be formed in suture 610 before or after the application of polymeric coatings 620a and 620b. First polymeric coating 620a may be positioned along only a portion of loop 612 and across only a portion of distal aperture 618. As shown, first polymeric coating 622a includes a plurality of coating apertures 622a, 622b, 622c. Second polymeric coating 620b may be positioned on a different section of distal end 611b and as shown is positioned on a portion of first and second overlapping sections 613, 614.

Barbs 630 may be arranged in any suitable pattern, for example, helical, linear, or randomly spaced. The pattern may be symmetrical or asymmetrical. The number, configuration, spacing and surface area of barbs 630 may vary depending upon the tissue in which suture 610 is used, as well as the composition and geometry of the material of elongate body 611. Additionally, the proportions of barbs 630 may remain relatively constant while the overall length of barbs 630 and the spacing of barbs 630 may be determined by the tissue being connected. For example, if suture 610 is to be used to connect the edges of a wound in skin or tendon, barbs 630 may be made relatively short and more rigid to facilitate entry into this rather firm tissue. Alternatively, if suture 610 is intended for use in fatty tissue, which is relatively soft, barbs 630 may be made longer and spaced further apart to increase the ability of suture 610 to grip the soft tissue.

The surface area of barbs 630 may also vary. For example, fuller-tipped barbs may be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example when a suture is used in tissue repair with differing layer structures. Use of the combination of large and small barbs with the same suture wherein barb sizes are customized for each tissue layer will ensure maximum anchoring properties. In particular embodiments, a single directional suture may have both large and small barbs; in other embodiments a bi-directional suture may have both large and small barbs. Barbs 630 may include geometrical shapes such as round, triangular, square, oblique, elliptical, octagonal, rectangular, and flat. In some embodiments, barbs 630 may be formed on loop 612 which allows movement of loop 612 through tissue in one direction but resists the withdrawal of suture 610 after loop 612 has been implanted in the tissue.

In embodiments, such as shown in FIG. 6, proximal end 613a of first section 613 may be angled to form a tapered surface 617. Tapered surface 617 angles downwardly towards proximal end 611a of looped suture 610. Tapered surface 617 forms an angle $\alpha$ relative to a longitudinal axis "X" of second section 614, between zero degrees (0°) and ninety degrees (90°), and preferably between about five degrees (5°) to about sixty degrees (60°). Tapered surface 617 facilitates insertion of loop 612 into or through tissue. Tapered surface 617 may be formed prior to, during or following the joining of first and second sections 613, 614. In one embodiment, tapered surface 617 is formed during the welding process using a die (not shown) having a cutting surface (not shown). In another embodiment, tapered surface 617 is formed by a blade (not shown). The blade used to form tapered surface 617 may be heated, ultrasonically vibrated or otherwise adapted to facilitate cutting of thread 611. Tapered surface 617 of first section 613 may be formed such that joined segment 615 extends beyond first section 613 of elongate body 611. In this manner, tapered surface 617 forms a smooth transition with second section 614 of elongate body 611.

Although shown having a substantially planar taper, tapered surface 617 may include any number of configurations. For example, FIGS. 7A-9C illustrate alternate embodiments, including a beveled tapered surface 717a (FIGS. 7A-7C), a laterally and longitudinally concave tapered surface 817b (FIGS. 8A-8C), a laterally and longitudinally convex tapered surface 917c (FIGS. 9A-9C) or any combination thereof. Respective beveled, concave and convex tapered surfaces (collectively, contoured tapered surfaces 717, 817, 917, respectively) may be formed in a similar manner as planar tapered surface 617. That is, contoured tapered surfaces 717, 817, 917 may be formed during the welding process using a die (not shown) having an appropriately shaped cutting surface (not shown). Alternatively, contoured tapered surfaces 717, 817, 917 may be formed using a blade (not shown) having an appropriately shaped cutting surface. Tapered surface 617 may be selected depending on the tissue being sutured and/or the desired depth of penetration of loop 612 within the tissue.

In some embodiments, the proximal end of the overlapping first section may be perpendicular to the second overlapping section of the suture (see FIG. 5). In still other embodiments, the proximal end of the overlapping first section may form an angle which is greater than ninety degrees, wherein the polymeric coating may be applied in a manner which creates a tapered polymeric coating (see FIG. 4).

When fabricated from a degradable material, the sutures described herein maintain their structural integrity after implantation for a predetermined period of time, depending on the characteristics of the particular copolymer used. Such characteristics include, for example, the components of the copolymer, including both the monomers utilized to form the copolymer and any additives thereto, as well as the processing conditions (e.g., rate of copolymerization reaction, temperature for reaction, pressure, etc.), and any further treatment of the resulting copolymers, i.e., coating, sterilization, etc. The manufacturing parameters involved in the forming of the loop also affect the rate at which the suture is absorbed. The joint may absorb at a different rate from the remainder of the suture.

The formation of barbs on a suture body may be utilized to change the degradation time of the suture as described in U.S. patent application Ser. No. 11/556,002 filed on Nov. 2, 2006, entitled "Long Term Bioabsorbable Barbed Sutures", the entire contents of which are incorporated by reference herein.

In some embodiments, at least one bioactive agent may be combined with the sutures described herein. For example, a bioactive agent may be combined with the polymer used to form the suture, and/or a bioactive agent may be combined with the polymeric coating. The at least one agent may be freely released by the suture or may be chemically bound to the surface of the suture.

Suitable bioactive agents include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents include substances which are beneficial and tend to promote the healing process. For example, the looped sutures can be provided with a bioactive agent that will be deposited at the sutured site. The bioactive agent can be chosen for its antimicrobial properties, capability for promoting wound repair and/or tissue growth, or for specific indications such as thrombosis. In embodiments, combinations of such agents may be applied to the medical device of the present disclosure before, during, or after formation of barbs.

The term "antimicrobial agent" as used herein includes an agent which by itself or through assisting the immune system, helps the body destroy or resist microorganisms which may be pathogenic. An antimicrobial agent includes antibiotics, antiseptics, quorum sensing blockers, antifungals, anti-virals, surfactants, metal ions, antimicrobial proteins and peptides, antimicrobial polysaccharides, disinfectants and combinations thereof. Antimicrobial agents which are slowly released into the tissue can be applied in this manner to aid in combating clinical and sub-clinical infections in a surgical or trauma wound site. In embodiments, suitable antimicrobial agents may be soluble in one or more solvents.

In embodiments, the following bioactive agents may be used alone or in combination with other bioactive agents described herein: an anthracycline, doxorubicin, mitoxantrone, a fluoropyrimidine, a folic acid antagonist, methotrexate, mitoxantrone, quorum sensing blocker, brominated or halogenated furanones, a podophylotoxin, etoposide, camptothecin, a hydroxyurea, a platinum complex, cisplatin, doxycycline, metronidazole, trimethoprim-sulfamethoxazole, rifamycins like rifampin, a fourth generation penicillin (e.g., a ureidopenicillin a carboxypenicillin, meziocillin, piperacillin, carbenicillin, and ticarcillin, and an analogue or derivative thereof), a first generation cephalosporin (e.g., cephazolin sodium, cephalexin, cefazolin, cephapirin, and cephalothin), a carboxypenicillin (e.g., ticarcillin), a second generation cephalosporin (e.g., cefuroxime, cefotetan, and cefoxitin), a third generation cephalosporin (e.g., naxcel, cefdinir, cefoperazone, ceftazidime, ceftriaxone, and cefotaxime), polyvinyl pyrrolidone (PVP), a fourth generation cephalosporin (e.g., cefepime), a monobactam (e.g., aztreonam), a carbapenem (e.g., imipenem, ertapenem and meropenem), an aminoglycoside (e.g., streptomycin, gentamicin, tobramycin, and amikacin), an MSL group member (e.g., a macrolide, a long acting macrolide, a lincosamide, a streptogramin, erythromycin, azithromycin, clindamycin, syneroid, clarithromycin, and kanamycin sulfate), tetracyclines like minocycline, fusidic acid, trimethoprim, metronidazole; a quinolone (e.g., ciprofloxacin, ofloxacin, gatifloxacin, moxifloxacin, levofloxacin, and trovafloxacin), a DNA synthesis inhibitor (e.g., metronidazole), a sulfonamide (e.g. sulfamethoxazole, trimethoprim, including cefixime, spectinomycin, tetracycline, nitrofurantoin, polymyxin B, and neomycin sulfate), beta-lactam inhibitors like sulbactam, chloramphenicol, glycopeptides like vancomycin, mupirocin, polyenes like amphotericin B, azoles like fluconazole, and other known antimicrobial agent known in the art.

Other suitable bioactive agents include one or more of the following: a fibrosing agent that promotes cell regeneration, a fibrosing agent that promotes angiogenesis, a fibrosing agent that promotes fibroblast migration, a fibrosing agent that promotes fibroblast proliferation, a fibrosing agent that promotes deposition of extracellular matrix, a fibrosing agent that promotes tissue remodeling, a fibrosing agent that is a diverticular wall irritant, silk (such as silkworm silk, spider silk, recombinant silk, raw silk, hydrolyzed silk, acid-treated silk, and acylated silk), talc, chitosan, bleomycin or an analogue or derivative thereof, connective tissue growth factor (CTGF), metallic beryllium or an oxide thereof, copper, saracin, silica, crystalline silicates, quartz dust, talcum powder, ethanol, a component of extracellular matrix, oxidized cellulose, polysaccharides, collagen, fibrin, fibrinogen, poly(ethylene terephthalate), poly(ethylene-co-vinylacetate), N-carboxybutylchitosan, an RGD protein, a polymer of vinyl chloride, cyanoacrylate, crosslinked poly (ethylene glycol)-methylated collagen, an inflammatory cytokine, TGFβ, PDGF, VEGF, TNFa, NGF, GM-CSF, IGF-a, IL-1, IL-8, IL-6, a growth hormone, a bone morphogenic protein, a cell proliferative agent, dexamethasone, isotretinoin, 17-β-estradiol, estradiol, diethylstibesterol, cyclosporine a, all-trans retinoic acid or an analogue or derivative thereof, wool (including animal wool, wood wool, and mineral wool), cotton, bFGF, polyurethane, polytetrafluoroethylene, activin, angiopoietin, insulin-like growth factor (IGF), hepatocyte growth factor (HGF), a colony-stimulating factor (CSF), erythropoietin, an interferon, endothelin-1, angiotensin II, bromocriptine, methylsergide, fibrosin, fibrin, an adhesive glycoprotein, proteoglycan, hyaluronan, secreted protein acidic and rich in cysteine (SPaRC), a thrombospondin, tenacin, a cell adhesion molecule, dextran based particles, an inhibitor of matrix metalloproteinase, magainin, tissue or kidney plasminogen activator, a tissue inhibitor of matrix metalloproteinase, carbon tetrachloride, thioacetamide, superoxide dismutase to scavenge tissue-damaging free radicals, tumor necrosis factor for cancer therapy, colony stimulating factor, interferon, interleukin-2 or other lymphokines to enhance the immune system, platelet rich plasma, thrombin, peptides such as self assembly peptide systems, amino acids such as radA based amino acids, hydrogels such as super absorbing hydrogel materials, combinations thereof, and so forth.

A wide variety of anti-angiogenic factors may be readily utilized within the context of the present disclosure. Representative examples include Anti-Invasive Factor; retinoic acid and derivatives thereof; paclitaxel a highly derivatized diterpenoid; Suramin; Tissue Inhibitor of Metalloproteinase-1; Tissue Inhibitor of Metalloproteinase-2; Plasminogen Activator Inhibitor-1; Plasminogen Activator Inhibitor-2; various forms of the lighter "d group" transition metals such as, for example, vanadium, molybdenum, tungsten, titanium, niobium, and tantalum species and complexes thereof; Platelet Factor 4; Protamine Sulphate (Clupeine); Sulphated Chitin Derivatives (prepared from queen crab shells); Sulphated Polysaccharide Peptidoglycan Complex (SP-PG) (the function of this compound may be enhanced by the presence of steroids such as estrogen, and tamoxifen citrate); Staurosporine; Modulators of Matrix Metabolism, including for example, proline analogs {[(L-azetidine-2-carboxylic acid (LACA), cishydroxyproline, d,L-3,4-dehydroproline, Thiaproline, $\alpha,\alpha$-dipyridyl, $\beta$-aminopropionitrile fumarate; MDL 27032 (4-propyl-5-(4-pyridinyl)-2(3H)-oxazolone; Methotrexate; Mitoxantrone; Heparin; Interferons; 2 Macroglobulin-serum; ChIMP-3; Chymostatin; $\beta$-Cyclodextrin Tetradecasulfate; Eponemycin; Camptothecin; Fumagillin Gold Sodium Thiomalate ("GST"); D-Penicillamine ("CDPT"); $\beta$-1-anticollagenase-serum; $\alpha$2-antiplasmin; Bisantrene; Lobenzarit disodium (N-(2)-carboxyphenyl-4-chloroanthronilic acid disodium or "CCA"; Thalidomide; Angostatic steroid; AGM-1470; carboxynaminolmidazole; metalloproteinase inhibitors such as BB94, analogues and derivatives thereof, and combinations thereof.

A wide variety of polymeric drugs may be readily utilized within the context of the present disclosure. Representative examples include steroidal anti-inflammatory agents, non-steroidal anti-inflammatory agents, and combinations thereof. Examples of the non-steroidal anti-inflammatory agent which may be used with the present disclosure are aspirin, indomethacin, ibuprofen, phenylbutazone, diflusinal, and combinations thereof.

Examples of the steroidal anti-inflammatory agent which may be used are glucocorticoids such as cortisone and hydrocortisone, betamethasone, dexamethasone, fluprednisolone, prednisone, methylprednisolone, prednisolone, triamcinolone, paramethasone, and combinations thereof.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents.

The looped sutures and/or polymeric coatings may also include, for example, biologically acceptable plasticizers, antioxidants and colorants, and other optional ingredients.

Bioactive agents may be applied onto the suture and/or the polymeric coating utilizing any method within the purview of one skilled in the art including, for example, spraying, dipping, brushing, rolling, wiping, painting, extruding, ultrasonics, and the like. In embodiments, a bioactive agent may be deposited within the barb angles, that is, the angle formed between the barbs and the elongate body of the sutures. This placement of the bioactive agent between the barbs and the elongate body of the sutures places the bioactive agent at precisely defined locations within a tissue wound closure, which thereby provides a unique controlled and sustained release dosage form.

The sutures may be dyed in order to increase the visibility of the suture in the surgical field. Any dye suitable for incorporation in medical devices may be used. Such dyes include, but are not limited to, carbon black, bone black, D&C Green No. 6, and D&C Violet No. 2. Filaments in accordance with the present disclosure may be dyed by adding dye in an amount up to about a few percent; in other embodiments, they may be dyed by adding dye in an amount of about 0.2%; in still further embodiments, the dye may be added in an amount from about 0.06% to about 0.08%.

In use, the looped sutures described herein may include a needle (not shown) on the proximal end thereof. The needle is inserted into and through a first and second flap of tissue. The looped suture may be pulled through the tissue until the proximal end of the first overlapping section contacts the tissue. Once a portion of the loop of the suture is received within the tissue, the proximal end of the suture may be inserted through the loop. The proximal end of the suture may then be pulled tight, thereby approximating the first and second tissue flaps towards one another. The proximal end of the suture may then be knotted or otherwise secured to the loop. In one embodiment, a knot may be formed in the proximal end to prevent the proximal end from withdrawing from the loop. In another embodiment, the proximal end of the suture may be tied directly to the loop.

EXAMPLE 1

A study was performed on 60 coated and uncoated looped sutures. Both sterilized and non-sterilized versions of the coated and uncoated looped sutures were equally tested.

Each of the looped sutures were made from a poly (glycolide-co-trimethylene carbonate) with the first and second overlapping portions of the looped suture ultrasonically welded to form the joint.

Thirty of the looped sutures remained uncoated and thirty of the looped sutures were dip-coated in a 5% solution of poly(glycolide-co-trimethylene carbonate) and allowed to dry. The dip-coated looped sutures included a web which span the distal aperture of the loop. The web was solid and not punctured.

Half of the coated and uncoated looped sutures were sterilized creating the following four groups: 15 uncoated, non-sterilized looped sutures; 15 uncoated, sterilized looped sutures; 15 coated non-sterilized looped sutures; and 15 coated, sterilized looped sutures.

Figure 10:
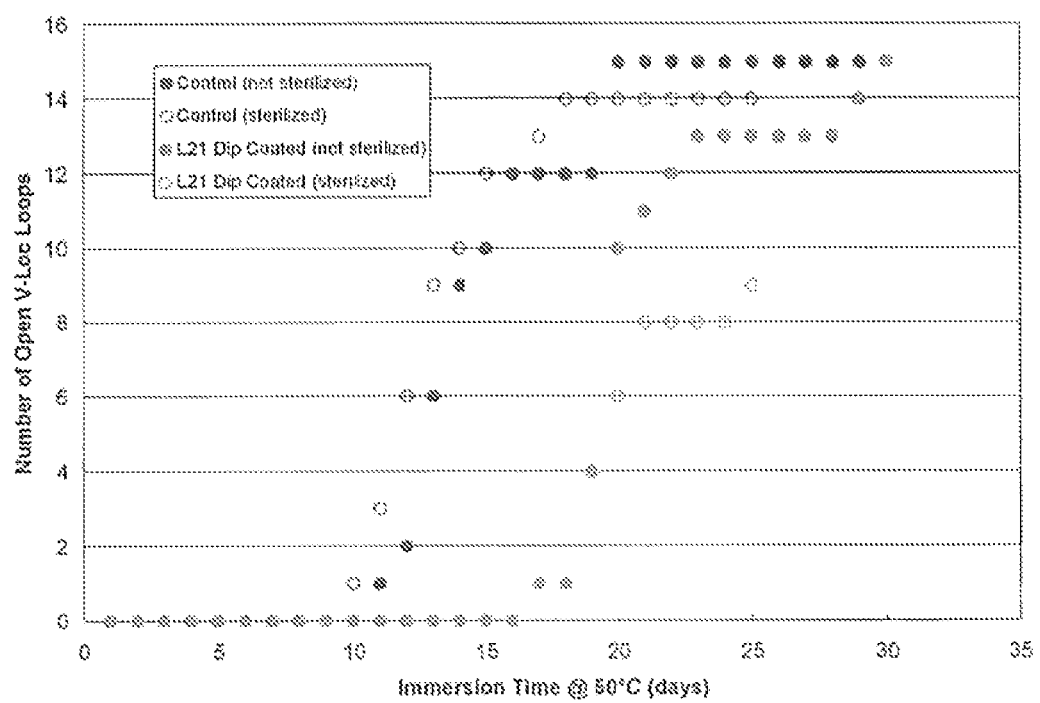
FIG. 10 is a Table comparing the number of open loops over time for coated and uncoated looped sutures after immersion in a buffer solution.

Each of the four groups were immersed in a buffer solution and maintained at a temperature of 50° C. to determine the amount of time needed for the looped suture to open and the overlapping sections to become unattached. The results are provided in FIG. 10.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A suture comprising:
an elongate body including a proximal section and a distal section, the distal section including a first section overlapping a second section, a loop, and a distal aperture defined within the loop; and
a polymeric coating positioned on only a portion of the distal section of the elongate body, the polymeric coating covering an entirety of the loop and only a portion of the first section overlapping the second section.

2. The suture of claim 1, wherein the elongate body comprises a biocompatible material.

3. The suture of claim 1, wherein the first and second sections are secured together by at least one method selected from the group consisting of glues, adhesives, solvents, heat, and ultrasonic energy.

4. The suture of claim 1, wherein the first and second sections are secured together by ultrasonic energy.

5. The suture of claim 1, wherein the first section further comprises a tapered end.

6. The suture of claim 5, wherein the tapered end of the first section angles downwardly towards the proximal section of the elongate body.

7. The suture of claim 1, wherein the polymeric coating comprises a material selected from the group consisting of polylactic acids, polyglycolic acids, polylactide-co-glycolide copolymers, polytrimethylene carbonate, poly-ϵ-caprolactone, poly-dioxanone, polyhydroxyalkanoates, polyphosphasenes, polypropylene fumarates, polyanhydrides, polyorthoesters, polyimides, polyurethanes, polyurethaneureas, perfluoroalkoxy polymers, florinated ethylene/propylene copolymers, polyanhydride esters, polysaccharides, polyethylene-lactone copolymers, polyethylene-polyorthoester copolymers, polymer drugs, hydrophilic vinyl polymers, phosphoryl cholines, hydroxamates, vinyl furanones, quarternary ammoniums, alkylene oxides, collagen, elastin, keratin, fibrin, and blends, copolymers, homopolymers, and combinations thereof.

8. The suture of claim 1, wherein the polymeric coating comprises copolymers of poly(glycolide-co-trimethylene carbonate).

9. The suture of claim 1, wherein the distal aperture defined within the loop allows the proximal section to pass through the distal aperture without passing through the polymeric coating.

10. The suture of claim 1, wherein the suture comprises a monofilament suture.

11. The suture of claim 1, wherein the polymeric coating is positioned across a portion of the distal aperture.

12. The suture of claim 11, wherein the polymeric coating positioned across a portion of the distal aperture comprises a film.

13. The suture of claim 11, wherein the polymeric coating positioned across a portion of the distal aperture comprises a web.

14. The suture of claim 11, wherein the polymeric coating positioned across a portion of the distal aperture is distal to, and in spaced relation from, the first section and the second section to reinforce the loop.

15. A suture comprising:
    an elongate body including a proximal section and a distal section, the distal section including a first section overlapping a second section, a loop, and a distal aperture defined within the loop; and
    a polymeric coating positioned on only the distal section of the elongate body, the polymeric coating completely covering the loop.

16. The suture of claim 15, wherein the polymeric coating extends over at least a portion of the first and second sections.

17. The suture of claim 16, wherein the polymeric coating completely covers the first and second sections.

18. The suture of claim 16, wherein the polymeric coating extends at least partially across the distal aperture.

19. The suture of claim 18, wherein the polymeric coating extends completely across the distal aperture.

20. The suture of claim 16, wherein the distal section of the elongate body includes a joint securing the first section to the second section.

* * * * *